United States Patent
Kim

(10) Patent No.: US 10,105,162 B2
(45) Date of Patent: Oct. 23, 2018

(54) SPINAL FIXING DEVICE

(71) Applicant: Mong-Joo Kim, Busan (KR)

(72) Inventor: Mong-Joo Kim, Busan (KR)

( * ) Notice: Subject to any disclaimer, the term of this patent is extended or adjusted under 35 U.S.C. 154(b) by 0 days.

(21) Appl. No.: 14/378,885

(22) PCT Filed: Feb. 14, 2013

(86) PCT No.: PCT/KR2013/001161
§ 371 (c)(1),
(2) Date: Aug. 14, 2014

(87) PCT Pub. No.: WO2013/122401
PCT Pub. Date: Aug. 22, 2013

(65) Prior Publication Data
US 2015/0045835 A1 Feb. 12, 2015

(30) Foreign Application Priority Data
Feb. 17, 2012 (KR) .......................... 10-2012-0016546

(51) Int. Cl.
*A61B 17/70* (2006.01)
(52) U.S. Cl.
CPC ...... *A61B 17/7002* (2013.01); *A61B 17/7037* (2013.01)
(58) Field of Classification Search
CPC combination set(s) only.
See application file for complete search history.

(56) References Cited

U.S. PATENT DOCUMENTS 8,182,512 B2 * 5/2012 Muhanna .............. A61F 2/4405
606/247
8,197,517 B1 * 6/2012 Lab .................... A61B 17/7037
606/268

(Continued)

FOREIGN PATENT DOCUMENTS

| KR | 1020100043149 A | 4/2010 |
| KR | 1020110016828 A | 2/2011 |
| KR | 1020110081875 A | 7/2011 |

*Primary Examiner* — Jan Christopher Merene
(74) *Attorney, Agent, or Firm* — STIP Law Group, LLC

(57) ABSTRACT

The present invention relates to a spinal fixing device in which a head portion of a bone screw to be inserted into a vertebra is bound to a housing, and the housing is fixed to a spine rod. The spinal fixing device includes: the housing having a seat portion inside and having a mounting groove for mounting the spine rod; a chuck to be inserted into the seat portion, in which a peripheral portion having an elastically changeable diameter and a curved inner circumferential surface is formed along the circumference of the chuck at one side; and the bone screw having a spherical head portion to be inserted into the peripheral portion, wherein a surface having a gradually varying diameter is formed on the inner circumferential surface of the seat portion and the outer circumferential surface of the peripheral portion is convex so as to allow the end of the peripheral portion to elastically shrink through the pressure generated between the peripheral portion and the seat portion by pressurization of the chuck by the spine rod, thereby restricting the rotation of the head portion. According to the present invention including said feature, the chuck is combined so as to restrict the head portion of the bone screw and has the peripheral portion having an elastically shrinkable diameter, and thus the movement between the screw and the housing is allowed according to the intention of an operator before being fixed to the spine rod and the movement between the (Continued)

housing and the bone screw can be more effectively inhibited when fixed to the spine rod.

8 Claims, 6 Drawing Sheets

(56) References Cited

U.S. PATENT DOCUMENTS

| | | | | |
|---|---|---|---|---|
| 8,663,298 B2* | 3/2014 | Keyer | ................ | A61B 17/7082 |
| | | | | 606/304 |
| 9,439,681 B2* | 9/2016 | Keyer | ................ | A61B 17/7037 |
| 2006/0142761 A1 | 6/2006 | Landry et al. | | |
| 2007/0049933 A1* | 3/2007 | Ahn | ................... | A61B 17/7037 |
| | | | | 606/279 |
| 2008/0147121 A1* | 6/2008 | Justis | ................ | A61B 17/7001 |
| | | | | 606/246 |
| 2009/0204155 A1* | 8/2009 | Aschmann | ......... | A61B 17/7037 |
| | | | | 606/264 |
| 2010/0198272 A1* | 8/2010 | Keyer | ................ | A61B 17/7037 |
| | | | | 606/302 |
| 2011/0213424 A1* | 9/2011 | Biedermann | ...... | A61B 17/7037 |
| | | | | 606/305 |
| 2012/0179212 A1* | 7/2012 | Jackson | ............. | A61B 17/7032 |
| | | | | 606/328 |

\* cited by examiner (a)

(b)

(c)

(d)

(e)

(f)

(g)

(h)

SPINAL FIXING DEVICE

CROSS-REFERENCE TO RELATED APPLICATION

This is a US National Phase Application of PCT patent Application No. PCT/KR2013/001161 having an International filing date of Feb. 14, 2013, which claims priority to Korean Patent Application No. 10-2012-0016546 filed on Feb. 17, 2012, the entireties of which are incorporated herein by reference.

FIELD OF THE INVENTION

The present invention relates to a spinal fixing device and more particularly to a spinal fixing device in which multiple bone screws (pedicle screws) are spaced apart from and coupled to a spine rod disposed along the vertebra, such that adjacent vertebrae are fixed apart from each other at a certain distance.

BACKGROUND OF THE INVENTION

The spine includes lumbar vertebra, thoracic vertebrae and cervical vertebrae, protects the spinal cord and nerve root, supports the body and relieves the external impact. The spine of the human body has a structure formed by stacking multiple vertebrae. The intervertebral disc is located between the vertebrae and evenly distributes the load and impact to the entire spine.

However, recently, spinal diseases continue to increase due to the lack of exercise and incorrect postures. The treatment of diseases related to the spine generally includes an indirect treatment using physical therapy and a direct treatment for correcting and fixing the spine by attaching a separate fixing device to the injured vertebrae.

There are various causes of spine injury. Among the causes, the bio-mechanic cause is known as the most likely cause. Therefore, for the purpose of the physical chiropractic of the injured spine, a spinal fixing device such as a pedicle screw is generally operated.

A general spinal fixing operation using the pedicle screw, that is, the above-mentioned direct treatment, is performed by inserting (at least two) pedicle screws into the vertebrae respectively and then by fixing and coupling the housing coupled with the each pedicle screw to the spine rod disposed approximately parallel with the longitudinal direction of the spine.

Meanwhile, the pedicle screw is divided into a mono type where the screw and the housing are integrally formed with each other and a polyaxial type where the screw and the housing are separately made such that a predetermined rotation is allowed between the screw and the housing, and then are coupled to each other.

The shape of the vertebra (into which the pedicle screw is inserted) is not constant according to patients and operation position. Therefore, at the time of the operation, the polyaxial type pedicle screw is widely used in order that a doctor is allowed to insert the pedicle screw more easily to a part into which the mono type pedicle screw cannot be inserted.

DETAILED DESCRIPTION OF THE INVENTION

Figure 1:
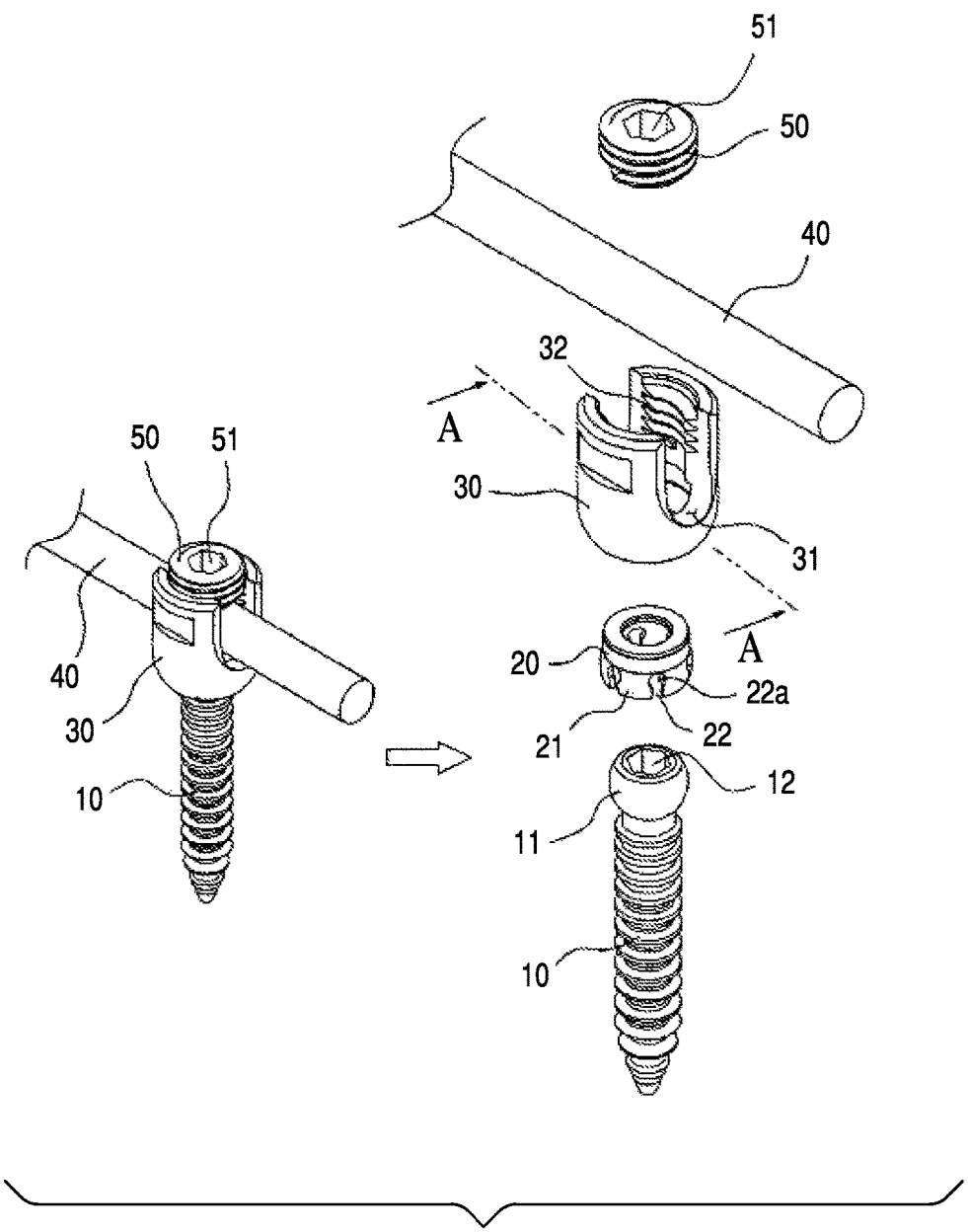
FIG. 1 is a perspective view showing that an assembled and disassembled spinal fixing device according to the embodiment of the present invention.

With regard to the mono type pedicle screw, after the housing and the screw are integrally molded and inserted into the vertebra, unnecessary shaking (or twisting) is not expected to occur between the housing and the screw. However, with regard to the polyaxial type pedicle screw, there exists a possibility that the shaking occurs between the housing and the screw in accordance with the load and impact which act on the vertebra due to patient's activity.

That is, in the existing polyaxial pedicle screw, a washer, etc., which is inserted within the housing by the fall of the spine rod and is fitted between the head portion and the spine rod, fixes the screw in a manner of pressing downwardly only the upper contact area of the head portion. However, the head portion of the screw is formed in the shape of a ball, so that when the contact area is small and the tightening torque of the fixing screw is insufficient, unintended twisting or bending is expected to occur between the housing and the screw by the sudden movement of the operation position, or by the load and external impact which act on the operation position.

Therefore, the present invention is to provide a spinal fixing device capable of allowing the movement of the housing coupled to the head portion of the screw before being coupled to the spine rod in order to provide the degree of freedom of the operation, and of preventing more efficiently the movement between the screw and the head portion after being coupled to the spine rod.

Technical Solution

The embodiment of the present invention provides a spinal fixing device in which a head portion of a bone screw to be inserted into a vertebra is bound to a housing, and the housing is fixed to a spine rod. The spinal fixing device includes: the housing having a seat portion inside and having a mounting groove for mounting the spine rod; a chuck to be inserted into the seat portion, in which a peripheral portion having an elastically changeable diameter and a curved inner circumferential surface is formed along the circumference of the chuck at one side; and the bone screw having a spherical head portion to be inserted into the peripheral portion, wherein a surface like a concave surface or an inclined surface having a gradually varying diameter is formed on the inner circumferential surface of the seat portion and the outer circumferential surface of the peripheral portion is convex so as to allow the end of the peripheral portion to elastically shrink through the pressure generated between the peripheral portion and the seat portion by pressurization of the chuck by the spine rod, thereby restricting the rotation of the head portion.

The peripheral portion may be divided into multiple pieces by incisions arranged along the circumference thereof. An end of the incision may have a bent shape, or an expansion part having an increased inner diameter may be formed at the end of the incision.

Meanwhile, the chuck is inserted within the housing in a direction opposite to the direction in which the spine rod is mounted. The seat portion includes: an entry portion which is formed at an entrance of the seat portion and has an inner diameter larger than a maximum outer diameter of the head portion of the bone screw; a transformation inducing portion which is connected to the entry portion and is comprised of a concave surface or an inclined tapered surface such that the diameter of the peripheral portion is gradually elastically transformed; and a coupling portion which is connected to the transformation inducing portion and provides a space allowing the diameter of the peripheral portion to be elastically expanded.

The coupling portion is comprised of a concave surface. The concave surface has a different center of curvature from that of the transformation inducing portion, so that a boundary is created between the coupling portion and the transformation inducing portion.

Also, the entry portion is comprised of a flat having a certain length along a longitudinal direction of the housing. A neck bent to be closely contacted with the entry portion is formed at the end of the peripheral portion.

Also, the head portion of the bone screw is formed to have a shape having an elliptical curvature in which a vertical length is larger than a horizontal length.

Meanwhile, the head portion of the bone screw is pressed to the inside of the peripheral portion and assembled after the chuck is inserted into the seat portion. A catching protrusion is formed within the housing in order to prevent the chuck from being separated.

Advantageous Effects

The chuck of the embodiment of the present invention can allow the movement between the bone screw and the housing in accordance with the operator's intention before the peripheral portion which is coupled to restrict the head portion of the bone screw and has an elastically changeable diameter is formed and fixed to the spine rod, and can restrict more efficiently the movement between the housing and the bone screw after being coupled to the spine rod.

The peripheral portion may be easily and elastically transformed by incisions arranged along the circumference thereof. The end of the incision may have an expansion part having an increased inner diameter, and then increase the fixing force by more efficiently inducing the elastic transformation.

Meanwhile, unlike the existing spinal fixing device in which a fixing jig structure is inserted from the top of the housing (the direction in which the spine rod is mounted), since there is no need to increase the inner diameter of the hole for inserting the fixing jig (since is no need to reduce the thickness of the housing), the rigidity of the housing is more improved than that of the existing housing.

Also, regarding the existing bone screw, when the outer diameter of the screw inserted into the vertebra is large (generally larger than 07.5), the head portion of the bone screw and the screw unit inserted into the vertebra are separated from each other and coupled. That is, the head portion is inserted from the top of the housing and the screw unit is inserted from the bottom of the housing, and then coupled to each other. Therefore, it is complicated and cumbersome to assembly them, and the integrally formed housing and screw are separated from each other, so that there is a structural weakness. However, in the present invention, since the bone screw coupled to the chuck is inserted into the bottom of the housing, the screw is integrally assembled to the housing irrespective of the size of the outer diameter of the screw unit (which is inserted into the vertebra). As a result, both simplicity and structural stability can be obtained.

Further, after the bone screw and the housing are coupled to each other, the head portion of the bone screw coupled to the chuck may partially protrude downward from the housing. Therefore, the range in which the bone screw moves is more increased than that of the existing structure.

Meanwhile, since the transformation inducing portion and the coupling portion, which have a mutually distinguishing boundary therebetween, are formed and more efficiently induce elastic expansion, restoration and elastic contraction of the diameter of the peripheral portion, the seat portion is able to more easily perform not only the chuck insertion but coupling and fixing of the bone screw.

Also, the entry portion of the end of the seat portion is formed flat, and the neck is formed on the end of the peripheral portion. Therefore, when the peripheral portion elastically shrinks, the chuck is induced to move in the vertical pressing direction. Therefore, the coupling force between the chuck and the bone screw is evenly distributed without leaning in a particular direction.

The head portion of the bone screw is elliptically formed and may be closely contacted with the inside of the chuck. That is, while the inside of the chuck, which is shrunk by pressing the spine rod, is changed from the spherical shape to the elliptical shape, the head portion of the bone screw according to the embodiment of the present invention is formed to have the elliptical shape, so that the head portion is closely fixed to larger area of the inside of the changed chuck. Accordingly, it is possible to obtain the stable fixing structure.

MODE FOR INVENTION

Hereafter, the spinal fixing device of the embodiment of the present invention will be described in more detail with reference to the drawings.

Referring to FIG. 1, a bone screw 10 of the embodiment of the present invention has a predetermined diameter and length in such a manner as to be inserted into the vertebra. A screw unit having a screw thread formed therein is formed on the outer circumferential surface of the bone screw 10. A head portion 11 is formed on the top of the screw unit in the form of a ball or an egg (an elliptical shape). The surface of the head portion 11 is spherical. Also, a wrench recess 12 in which a wrench is fitted is formed in the head portion 11.

The head portion 11 enters the inside of the chuck 20 and is coupled without being separated. The chuck 20 has a ring shape in which a hole allowing the wrench recess 12 of the head portion 11 to be exposed is formed in the top and bottom of the chuck. A peripheral portion 21 is formed along the circumference of the lower portion of the chuck. The diameter of the peripheral portion 21 can be elastically expanded.

The peripheral portion 21 is divided into multiple pieces by incisions 22 formed spaced apart from each other by a regular interval. A concave curved surface is formed on the inner circumferential surface (inner surface) of the peripheral portion 21 such that the head portion 11 is coupled and restricted after the inner diameter of the peripheral portion 21 is elastically expanded. The peripheral portion 21 may have a thin portion formed therein in order to be more easily elastically expanded. An expansion part 22a is formed by expanding or bending the end of the dug portion of the incision 22 according to the embodiment of the present invention. When a spine rod 40 presses the expansion part 22a, the expansion part 22a is elastically transformed and thus improves the coupling strength.

A seat portion 33 having a predetermined size is formed within a housing 30 into which the head portion 11 of the bone screw 10 and the chuck 20 are inserted.

Figure 2:
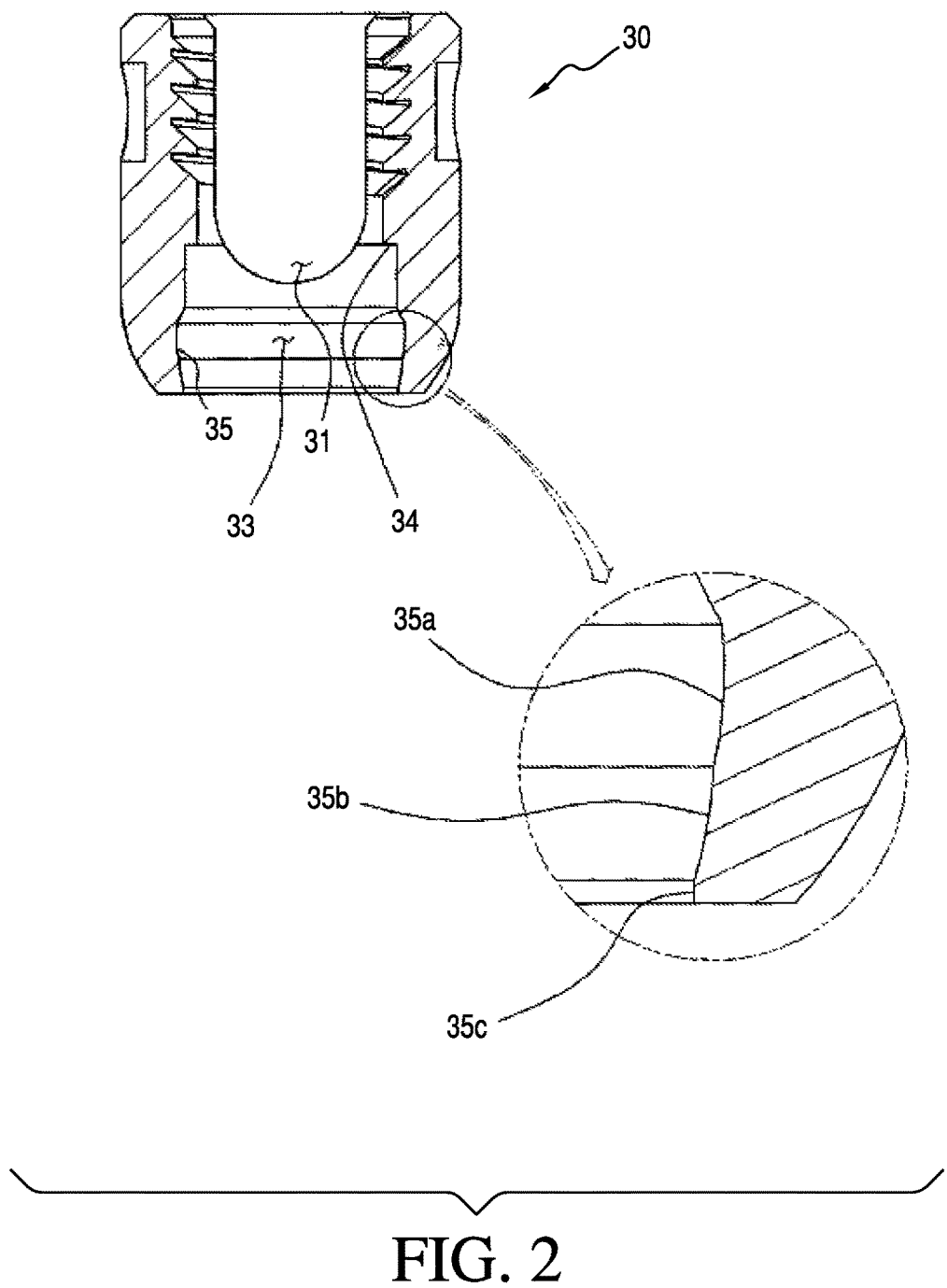
FIG. 2 shows a cross sectional view and a partial enlarged view taken along line A-A' shown in FIG. 1.

Referring to FIG. 2, the housing 30 has upper and lower openings. A mounting recess 31 on which the spine rod 40 is mounted is formed on one side of the housing 30. A female screw thread 32 having a certain length is formed on the inner circumferential surface of the upper portion of the housing 30 such that a fixing screw 50 is fitted to the female screw thread 32. The lower portion of the housing 30 includes the seat portion 33, that is, a space having a predetermined size and allowing the chuck 20 to be fitted and fixed thereto and includes a catching protrusion 34 for preventing the chuck 20 from being separated upward.

The chuck 20 enters the bottom of the seat portion 33, that is, the opposite side to the spine rod 40 and is inserted into the seat portion 33. The seat portion 33 is divided into an entry portion 35c, a transformation inducing portion 35b and a coupling portion 35a according to the shape and function of an inner circumferential surface 35.

The entry portion 35c is formed flat at the entrance of the seat portion 33. The inner diameter of the entry portion 35c is formed to be larger than the maximum outer diameter of the head portion 11 of the bone screw 10.

Meanwhile, when the chuck 20 is inserted, the peripheral portion 21 is entered with the elastically contracted diameter. The transformation inducing portion 35b connected to the entry portion 35c is comprised of a surface like a concave surface or an inclined tapered surface having a gradually varying diameter such that the diameter of the peripheral portion 21 is gradually elastically transformed.

Therefore, when the peripheral portion 21 passes through the transformation inducing portion 35b, in a case where the chuck 20 enters the seat portion 33, the diameter of the peripheral portion 21 is gradually expanded through the elastic restoration, so that the chuck 20 is restricted within the housing 30. In a case where the chuck 20 is pressed downward by the spine rod 40, the diameter of the peripheral portion 21 is gradually contracted and shrunk by the pressure between the transformation inducing portion 35b and the peripheral portion 21.

The coupling portion 35a is connected to the transformation inducing portion 35b and has an inner diameter allowing the diameter of the peripheral portion 21 to be elastically expanded when the head portion 11 of the bone screw 10 is coupled to the chuck 20. The coupling portion 35a is comprised of a concave surface having a different center of curvature from that of the transformation inducing portion 35b, so that a boundary is created between them.

Figure 3:
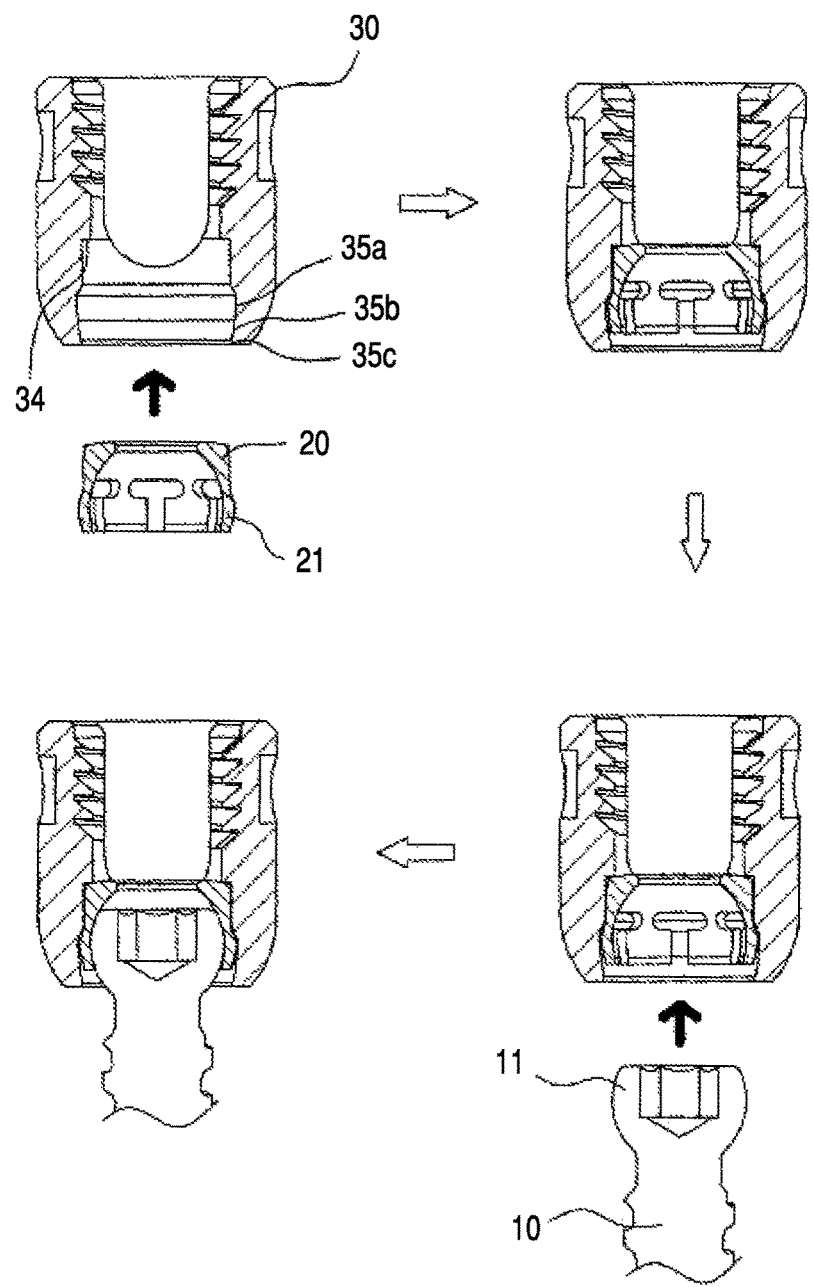
FIG. 3 are cross sectional views showing sequentially that the chuck and the bone screw are coupled to the housing in accordance with the embodiment of the present invention.

Therefore, as shown in FIG. 3, the chuck 20 enters the seat portion 33 with the elastically contracted diameter of the peripheral portion 21. Then, the diameter of the peripheral portion 21 is elastically restored to the original size within the coupling portion 35a. Here, the final entry position of the seat portion 33 is determined as the coupling portion 35a by the catching protrusion 34 formed on the seat portion 33.

Also, the head portion 11 of the bone screw 10 passes through the entry portion 35c and is inserted inside the peripheral portion 21. The diameter of the peripheral portion 21 is elastically expanded within the coupling portion 35a by the insertion of the head portion 11. After the head portion 11 is fully inserted, the diameter of the peripheral portion 21 is restored to the original size thereof. In this state, the bone screw 10 is rotatable (according to the will of the operator) and is restricted within the chuck 20 without being separated.

Figure 4:
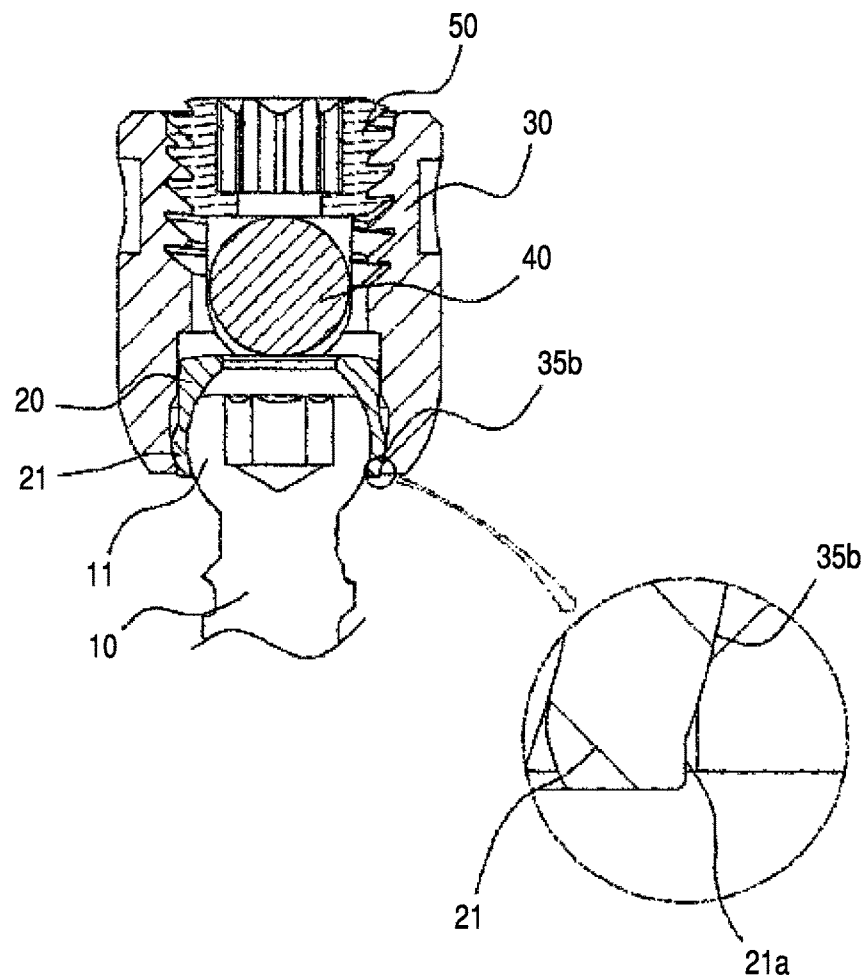
FIG. 4 shows a cross sectional view and a partial enlarged view showing that, after the spine rod is mounted in the housing, the chuck is pressed by tightening the fixing screw, so that the peripheral portion is shrunk.

Meanwhile, as described above, the entry portion 35c is comprised of a flat having a certain length along the longitudinal direction of the housing 30. As shown in FIG. 4, a neck 21a bent to be closely contacted with the entry portion 35c is formed at the end of the peripheral portion 21. Due to the formation of the neck 21a, the chuck 20 is induced to fall downwardly without leaning in a particular direction when the spine rod 40 is pressed.

Figure 5:
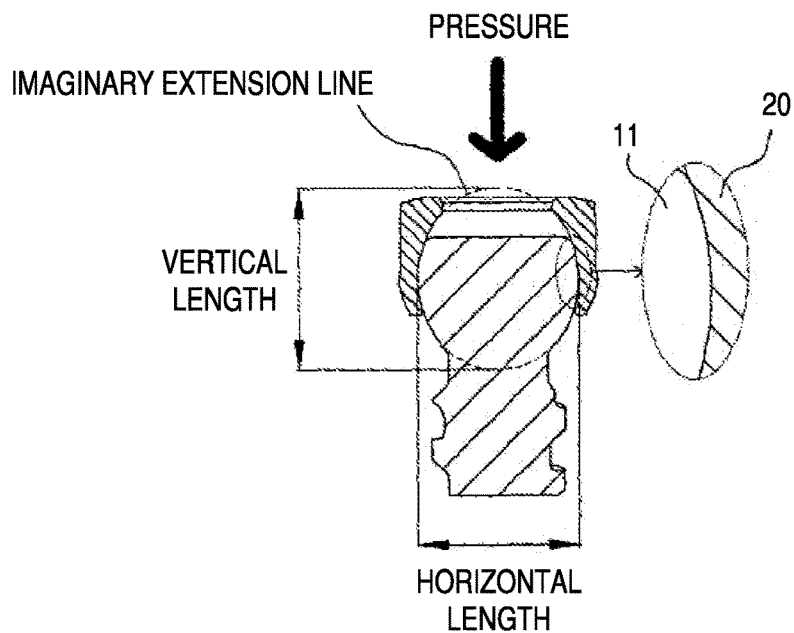
FIG. 5 is a cross sectional view comparing and showing how closely the head portion of the bone screw is contacted with the inside of the chuck in accordance with the shape of the head portion of the bone screw.
Figure 5:
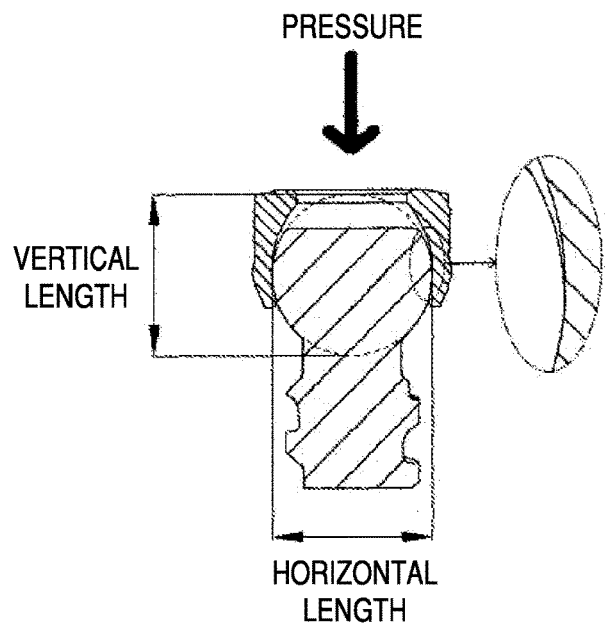

As shown in FIG. 5, the head portion 11 of the bone screw 10 according to the embodiment of the present invention may be formed to have a shape having an elliptical curvature in which the vertical length is larger than the horizontal length such that the head portion 11 of the bone screw 10 is closely contacted with a larger area by the elastic transformation of the shape of the chuck 20, thereby improving the coupling force.

Figure 6:
FIG. 6 shows modified examples obtained by forming the expansion part in various shapes in the chuck according to the embodiment of the present invention.
Figure 6:
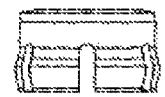
Figure 6:
Figure 6:
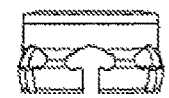
Figure 6:
Figure 6:
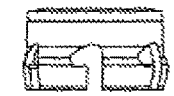
Figure 6:
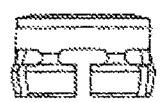
Figure 6:
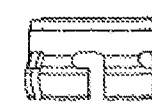
Figure 6:

As shown in (a) to (h) of FIG. 6, a structure having various incisions and expansion parts can be manufactured.

The embodiments of the present invention disclosed in the specification and drawings merely provide specific examples for helping the understanding of the present invention and are not intended to limit the scope of the present invention.

It is clearly understood by those skilled in the art that the above-mentioned embodiments can be also modified based on the spirit of the present invention.

| Description of reference numerals | |
|---|---|
| 10: screw | 11: head portion |
| 20: chuck | 21: peripheral portion |
| 30: housing | 40: spine rod |
| 50: fixing screw | |

I claim:

1. A spinal fixing device in which a head portion of a bone screw to be inserted into a vertebra is bound to a housing, and in which the housing is fixed to a spine rod, the spinal fixing device comprising:
   a housing having a central longitudinal axis, a seat portion inside and having a mounting groove for mounting the spine rod;
   a chuck to be inserted into the seat portion, in which a peripheral portion having an elastically changeable diameter and a curved inner circumferential surface is formed along the circumference of the chuck at one side; and
   a bone screw having a threaded shank that integrally terminates at one end in a spherical head portion to be inserted into the peripheral portion,
   wherein a surface having a gradually varying diameter is formed on the inner circumferential surface of the seat portion, and the outer circumferential surface of the peripheral portion is convex such that an end of the peripheral portion is elastically shrunk through the pressure generated between the peripheral portion and the seat portion by pressurization of the chuck by the spine rod, so that the rotation of the head portion is restricted, wherein the seat portion comprises:

a transformation inducing portion having a gradually varying diameter such that a diameter of the peripheral portion is gradually elastically transformed at an entrance of the seat portion; and a coupling portion which is connected to the transformation inducing portion and provides a space allowing the diameter of the peripheral portion to be elastically expanded, wherein an entry portion is formed at the entrance of the seat portion and has an inner diameter larger than a maximum outer diameter of the head portion of the bone screw, and wherein the entry portion is comprised of a flat having a certain length extending substantially parallel to the central longitudinal axis, and wherein a neck is formed that extends substantially parallel to the central longitudinal axis at a lower end of the peripheral portion and is capable of being close to the entry portion when the peripheral portion is in the space.

2. The spinal fixing device of claim 1, wherein the peripheral portion is divided into multiple pieces by incisions arranged along the circumference thereof.

3. The spinal fixing device of claim 2, wherein an end of the incision has a bent shape, or an expansion part having an increased inner diameter is formed at the end of the incision.

4. The spinal fixing device of claim 3, wherein the chuck is inserted into the seat portion within the housing in a direction opposite to the direction in which the spine rod is mounted, and wherein the bone screw is restricted and coupled by fitting the head portion to the inside of the peripheral portion in the same direction as the insertion direction of the chuck.

5. The spinal fixing device of claim 1, wherein the head portion of the bone screw is pressed to the inside of the peripheral portion and assembled after the chuck is inserted into the seat portion, and wherein a catching protrusion is formed within the housing in order to prevent the chuck from being separated.

6. The spinal fixing device of claim 1, wherein an upper outer surface of the chunk directly and slidably engages an upper inner surface of the housing.

7. The spinal fixing device of claim 1, wherein an outer surface of the peripheral portion of the chunk slidably engages an inner surface of the coupling portion prior to the elastic shrinking of the peripheral portion by pressurization of the chunk by the spine rod.

8. The spinal fixing device of claim 1, wherein the head portion is axially aligned with the threaded shank of the bone screw.

* * * * *